United States Patent
Nieendick et al.

(10) Patent No.: US 6,835,700 B1
(45) Date of Patent: Dec. 28, 2004

(54) HIGHLY CONCENTRATED FREE-FLOWING PEARLY LUSTRE CONCENTRATES

(75) Inventors: Claus Nieendick, Krefeld (DE); Karl Heinz Schmid, Mettmann (DE); Mirella Nalborczyk, Duesseldorf (DE)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 0 days.

(21) Appl. No.: 10/009,285
(22) PCT Filed: Apr. 28, 2000
(86) PCT No.: PCT/EP00/03854
§ 371 (c)(1), (2), (4) Date: Nov. 6, 2001
(87) PCT Pub. No.: WO00/68350
PCT Pub. Date: Nov. 16, 2000

(30) Foreign Application Priority Data

May 7, 1999 (DE) .......................... 199 21 186

(51) Int. Cl.$^7$ ................................. A61K 7/00
(52) U.S. Cl. ................. 510/119; 510/121; 510/124; 510/125; 510/123
(58) Field of Search ............... 510/124, 128, 510/123, 119, 121, 125, 130, 424, 426, 428; 424/70.1, 70.19, 70.21, 70.31; 516/77, 928

(56) References Cited

U.S. PATENT DOCUMENTS

| | | | |
|---|---|---|---|
| 4,172,887 A | 10/1979 | Vanlerberghe et al. | |
| 4,777,038 A | 10/1988 | Scheuffgen | |
| 5,403,508 A | 4/1995 | Reng et al. | |
| 5,705,169 A | 1/1998 | Stein et al. | |
| 5,711,899 A | 1/1998 | Kawa et al. | |
| 5,730,960 A | 3/1998 | Stein et al. | |
| 5,945,091 A | 8/1999 | Habeck et al. | |
| 6,193,960 B1 | 2/2001 | Metzger et al. | |
| 6,228,831 B1 * | 5/2001 | Ansmann et al. | 510/416 |
| 6,235,702 B1 | 5/2001 | Ansmann et al. | |
| 6,555,101 B1 * | 4/2003 | Kahre et al. | 424/70.1 |

FOREIGN PATENT DOCUMENTS

| | | |
|---|---|---|
| DE | 1 165 574 A | 3/1964 |
| DE | 20 24 051 C3 | 12/1971 |
| DE | 38 43 572 A1 | 6/1990 |
| DE | 41 03 551 A1 | 8/1992 |
| DE | 196 21 681 A1 | 12/1997 |
| DE | 198 01 231 C1 | 4/1999 |
| EP | 0 181 773 A2 | 5/1986 |
| EP | 0 205 922 A2 | 12/1986 |
| EP | 0 285 389 B1 | 9/1992 |
| EP | 0 569 028 A2 | 11/1993 |
| EP | 0 581 193 A2 | 2/1994 |
| EP | 0 569 843 B1 | 11/1995 |
| EP | 0 684 302 A1 | 11/1995 |
| EP | 0 693 471 B1 | 1/1998 |
| EP | 0 818 450 A1 | 1/1998 |
| FR | 2 252 840 A | 8/1975 |
| GB | 962919 A | 7/1964 |
| GB | 1 333 475 A | 10/1973 |

OTHER PUBLICATIONS

Ansmann, et al., "P rlglanz in modernen, tensidhaltigen Formuli rungen", Parfümerie und Kosmetik, vol. 75, (1994), pp. 578–580.

Todd, et al., "Volatile Silicone Fluids For Cosmetic Formulations", Cosmetics and Toiletries, vol. 91, (Jan., 1976), pp. 29–32.

Lochhead, et al., "Encyclopedia of Polymers and Thickeners for Cosmetics", Cosmetics and Toiletries, vol. 108, (May, 1993), pp. 95–114, 116–124, 127–130, 132–135.

Finkel, "Formulierung Kosmetischer Sonnenschutzmittel", SÖFW–Journal, vol. 122, (1996), pp. 543–546 & 548.

"Kosmetische Färbemittel", Farbstoffkommission der Deutschen Forschungsgemeinschaft, Verlag Chemie, Weinheim, (1984), pp. 81–106.

* cited by examiner

Primary Examiner—Necholus Ogden
(74) Attorney, Agent, or Firm—Aaron R. Ettelman; Steven J. Trzaska; Daniel S. Ortiz

(57) ABSTRACT

A highly concentrated flowable pearlizing concentrate is comprised of: (a) from about 25 to about 45% by weight of a pearlizing wax; (b) from about 25 to about 40% by weight of nonionic, amphoteric, zwitterionic and/or cationic emulsifier and; (c) from about 0.5 to about 15% by weight of a polyol ester and the remainder water. The sum of components (a), (b) and (c) is at least 55% by weight. The concentrates are useful cosmetic applications such as in hair shampoos and shower gels.

9 Claims, No Drawings

HIGHLY CONCENTRATED FREE-FLOWING PEARLY LUSTRE CONCENTRATES

BACKGROUND OF THE INVENTION

This invention relates to highly concentrated pearlizing concentrates containing pearlizing waxes, special emulsifier mixtures and optionally polyols, to a process for their production and to the use of certain co-emulsifiers as viscosity adjusters for the production of pearlizing concentrates with a high active-substance content.

PRIOR ART

For centuries, the softly shimmering luster of pearls has held a particular fascination for human beings. It is therefore no wonder that manufacturers of cosmetic preparations endeavour to give their products an attractive, valuable and rich appearance. The first pearlescence used in cosmetics in the middle ages was a pearlizing paste of natural fish scales. At the beginning of the present century, it was discovered that bismuth oxide chlorides were also capable of producing pearlescence. By contrast, pearlizing waxes, particularly of the glycol monofatty acid ester and difatty acid ester type, are of importance in modern cosmetics, being used mainly for the production of pearlescence in hair shampoos and shower gels. An overview of modern pearlizing formulations was published by A. Ansmann and R. Kawa in Parf. Kosm., 75, 578 (1994).

Various formulations capable of providing surface-active products with the required pearlescence are known from the prior art. For example, German patent applications DE 38 43 572 A1 and DE 41 03 551 A1 (Henkel) describe pearlizing concentrates in the form of free-flowing aqueous dispersions containing 15 to 40% by weight of pearlizing components, 5 to 55% by weight of emulsifiers and 0.1 to 5% by weight or 15 to 40% by weight of polyols. The pearlizing waxes are acylated polyalkylene glycols, monoalkanolamides, linear saturated fatty acids or ketosulfones. European patents EP 0 181 773 B1 and EP 0 285 389 B1 (Procter & Gamble) describe shampoo compositions containing surfactants, non-volatile silicones and pearlizing waxes. European patent application EP 0 205 922 A2 (Henkel) relates to free-flowing pearlizing concentrates containing 5 to 15% by weight of acylated polyglycols, 1 to 6% by weight of fatty acid monoethanolamides and 1 to 5% by weight of nonionic emulsifiers. According to the teaching of European patent EP 0 569 843 B1 (Hoechst), nonionic, free-flowing pearlizing dispersions can also be obtained by preparing mixtures of 5 to 30% by weight of acylated polyglycols and 0.1 to 20% by weight of selected nonionic surfactants. In addition, European patent application EP 0 581 193 A2 (Hoechst) describes free-flowing, preservative-free pearlizing dispersions containing acylated polyglycol ethers, betaines, anionic surfactants and glycerol. Finally, European patent application EP 0 684 302 A1 (Th. Goldschmidt) relates to the use of polyglycerol esters as crystallization aids for the production of pearlizing concentrates.

Despite the large number of formulations, there is a constant need on the market for new pearlizing concentrates which, even with extremely high active substance contents, are still flowable, have excellent performance properties, allow the use of critical ingredients, such as silicones for example, without the stability of the formulations being impaired, and produce other positive effects in the end formulations. Accordingly, the problem addressed by the present invention was to provide new pearlizing concentrates which would satisfy the complex requirement profile mentioned above.

DESCRIPTION OF THE INVENTION

The present invention relates to highly concentrated flowable pearlizing concentrates containing (a) 25 to 45, preferably 30 to 40% by weight of pearlizing waxes, (b) 25 to 40, preferably 30 to 35% by weight of nonionic, amphoteric, zwitterionic and/or cationic emulsifiers and (c) 0.5 to 15, preferably 1 to 10% by weight of polyol esters with the provisos that the quantities shown add up to 100% by weight with water and optionally other auxiliaries and additives and the sum of components (a), (b) and (c) is at least 55, preferably at least 60 and more particularly 65 to 70% by weight.

It has surprisingly been found that the use of polyol esters allows the production of pearlizing concentrates which have a distinctly increased active substance content (corresponding to the sum of pearlizing waxes and emulsifiers/co-emulsifiers) in relation to known preparations, but are still flowable at room temperature. The new pearlizing concentrates are particularly finely particulate and provide water-based surfactant-containing preparations with a particularly dense and sparkling pearlescence. If they are used for the production of hair treatment preparations, they additionally improve the shine and softness of the washed hair. Silicone compounds may readily be incorporated.

Pearlizing Waxes

Suitable pearlizing waxes are, for example, alkylene glycol esters, fatty acid alkanolamides, partial glycerides, esters of polybasic, optionally hydroxysubstituted carboxylic acids, fatty alcohols, fatty acids, fatty ketones, fatty aldehydes, fatty ethers, fatty carbonates, ring opening products of olefin epoxides and mixtures thereof.

The alkylene glycol esters which form component (a1) are normally monoesters and/or diesters of alkylene glycols corresponding to formula (III):

$$R^5CO(OA)_nOR^6 \quad\quad\quad (III)$$

in which $R^5CO$ is a linear or branched, saturated or unsaturated acyl group containing 6 to 22 carbon atoms, $R^6$ is hydrogen or has the same meaning as $R^5CO$ and A is a linear or branched alkylene group containing 2 to 4 carbon atoms and n is a number of 1 to 5. Typical examples are monoesters and/or diesters of ethylene glycol, propylene glycol, diethylene glycol, dipropylene glycol, triethylene glycol or tetraethylene glycol with fatty acids containing 6 to 22 and preferably 12 to 18 carbon atoms, such as caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and technical mixtures thereof. Ethylene glycol monostearate and/or distearate is/are particularly preferred.

Fatty acid alkanolamides suitable as pearlizing waxes of group (a2) correspond to formula (IV):

$$R^7CO-NR^8-B-OH \quad\quad\quad (IV)$$

in which $R^7CO$ is a linear or branched, saturated or unsaturated acyl group containing 6 to 22 carbon atoms, $R^8$ is hydrogen or an optionally hydroxy-substituted alkyl group containing 1 to 4 carbon atoms and B is a linear or branched alkylene group containing 1 to 4 carbon atoms. Typical examples are condensation products of ethanolamine, methyl ethanolamine, diethanolamine, propanolamine, methyl propanolamine and dipropanolamine and mixtures thereof with caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and technical mixtures thereof. Stearic acid ethanolamide is particularly preferred.

Partial glycerides which have pearlizing properties and which form component (a3) are monoesters and/or diesters of glycerol with linear, saturated fatty acids, i.e. for example caproic acid, caprylic acid, capric acid, lauric acid, myristic acid, palmitic acid, palmitoleic acid, stearic acid, behenic acid and technical mixtures thereof. They correspond to formula (V):

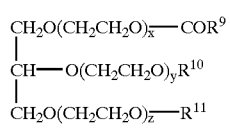

(V)

in which $R^9CO$ is a linear, saturated acyl group containing 6 to 22 carbon atoms, $R^{10}$ and $R^{11}$ independently of one another represent hydrogen or have the same meaning as $R^9CO$, x, y and z together stand for 0 or for a number of 1 to 30 and X is an alkali or alkaline earth metal, with the proviso that at least one of the two substituents $R^{10}$ and $R^{11}$ is hydrogen. Typical examples are lauric acid monoglyceride, lauric acid diglyceride, coconut fatty acid monoglyceride, coconut fatty acid triglyceride, palmitic acid monoglyceride, palmitic acid triglyceride, stearic acid monoglyceride, stearic acid diglyceride, tallow fatty acid monoglyceride, tallow fatty acid di-glyceride, behenic acid monoglyceride, behenic acid diglyceride and technical mixtures thereof which may still contain small quantities of triglyceride from the production process.

Other suitable pearlizing waxes which form component (a4) are esters of polybasic, optionally hydroxy substituted carboxylic acids with fatty alcohols containing 6 to 22 carbon atoms. The acid component of these esters may be selected, for example, from malonic acid, maleic acid, fumaric acid, adipic acid, sebacic acid, azelaic acid, dodecanedioic acid, phthalic acid, isophthalic acid and, more particularly, succinic acid and also malic acid, citric acid and, more particularly, tartaric acid and mixtures thereof. The fatty alcohols contain 6 to 22, preferably 12 to 18 and more preferably 16 to 18 carbon atoms in the alkyl chain. Typical examples are caproic alcohol, caprylic alcohol, 2-ethylhexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol and technical mixtures thereof. The esters may be present as full or partial esters; monoesters and, above all, diesters of carboxylic or hydroxycarboxylic acids preferably being used. Typical examples are succinic acid mono- and dilauryl ester, succinic acid mono- and dicetearyl ester, succinic acid mono- and distearyl ester, tartaric acid mono- and dilauryl ester, tartaric acid mono- and dicocoalkyl ester, tartaric acid mono- and dicetearyl ester, citric acid mono-, di- and trilauryl ester, citric acid mono-, di- and tricocoalkyl ester and citric acid mono-, di- and tricetearyl ester.

Another group of pearlizing waxes (a5) are fatty alcohols and/or fatty acids corresponding to formula (VI):

$R^{12}OH$ (VI)

in which $R^{12}$ is a linear optionally hydroxy-substituted alkyl group and/or acyl group containing 16 to 48 and preferably 18 to 36 carbon atoms. Typical examples of suitable alcohols are cetearyl alcohol, hydroxystearyl alcohol, behenyl alcohol and oxidation products of long-chain paraffins. Examples of acids are stearic acid, hydroxystearic acid and, more particularly behenic acid in a purity of preferably more than 90% by weight.

Fatty ketones suitable as component (a6) preferably correspond to formula (VII):

$R^{13}$—CO—$R^{14}$ (VII)

in which $R^{13}$ and $R^{14}$ independently of one another represent alkyl and/or alkenyl groups containing 1 to 22 carbon atoms, with the proviso that they contain a total of at least 24 and preferably 32 to 48 carbon atoms. The ketones may be prepared by known methods, for example by pyrolysis of the corresponding fatty acid magnesium salts. The ketones may be symmetrical or non-symmetrical, although the two substituents $R^{13}$ and $R^{14}$ preferably differ from one another by only one carbon atom and are derived from fatty acids containing 16 to 22 carbon atoms. Stearone is distinguished by particularly advantageous pearlizing properties.

Fatty aldehydes (a7) suitable as pearlizing waxes preferably correspond to formula (VIII):

$R^{15}COH$ (VIII)

in which $R^{15}CO$ is a linear or branched acyl group containing 24 to 48 and preferably 28 to 32 carbon atoms.

Other suitable pearlizing waxes (a8) are fatty ethers corresponding to formula (IX):

$R^{16}$—O—$R^{17}$ (IX)

in which $R^{16}$ and $R^{17}$ independently of one another represent alkyl and/or alkenyl groups containing 1 to 22 carbon atoms, with the proviso that they contain a total of at least 24 and preferably 32 to 48 carbon atoms. Fatty ethers of the type mentioned are normally prepared by acidic condensation of the corresponding fatty alcohols. Fatty ethers with particularly advantageous pearlizing properties are obtained by condensation of fatty alcohols containing 16 to 22 carbon atoms such as, for example, cetyl alcohol, cetearyl alcohol, stearyl alcohol, isostearyl alcohol, oleyl alcohol, behenyl alcohol and/or erucyl alcohol.

Other suitable pearlizing waxes (a9) are fatty carbonates corresponding to formula (X):

$R^{18}O$—CO—$OR^{19}$ (X)

in which $R^{18}$ and $R^{19}$ independently of one another are alkyl and/or alkenyl groups containing 1 to 22 carbon atoms, with the proviso that they contain a total of at least 24 and preferably 32 to 48 carbon atoms. The substances are obtained by transesterifying dimethyl or diethyl carbonate, for example, with the corresponding fatty alcohols by methods known per se. Accordingly, the fatty carbonates may be symmetrical or non-symmetrical However, carbonates in which $R^{18}$ and $R^{19}$ are the same and represent alkyl groups containing 16 to 22 carbon atoms are preferably used. Transesterification products of dimethyl or diethyl carbonate with cetyl alcohol, cetearyl alcohol, stearyl alcohol, isostearyl alcohol, oleyl alcohol, behenyl alcohol and/or erucyl alcohol in the form of their monoesters and diesters and technical mixtures thereof are particularly preferred.

Finally, the ring-opening products which form group (a10) are known substances which are normally obtained by acid-catalyzed reaction of terminal or internal olefin epoxides with aliphatic alcohols. The reaction products preferably correspond to formula (XI):

in which $R^{20}$ and $R^{21}$ represent hydrogen or an alkyl group containing 10 to 20 carbon atoms, with the proviso that the sum total of carbon atoms of $R^{20}$ and $R^{21}$ is between 10 and 20 and $R^{22}$ is an alkyl and/or alkenyl group containing 12 to 22 and/or the residue of a polyol containing 2 to 15 carbon atoms and 2 to 10 hydroxyl groups. Typical examples are ring-opening products of α-dodecene epoxide, α-hexadecene epoxide, α-octadecene epoxide, α-eicosene epoxide, α-docosene epoxide, i-dodecene epoxide, i-hexadecene epoxide, i-octadecene epoxide, i-eicosene epoxide and/or i-docosene epoxide with lauryl alcohol, cocofatty alcohol, myristyl alcohol, cetyl alcohol, cetearyl alcohol, stearyl alcohol, isostearyl alcohol, oleyl alcohol, elaidyl alcohol, petroselinyl alcohol, linolyl alcohol, linolenyl alcohol, behenyl alcohol and/or erucyl alcohol. Ring opening products of hexa- and/or octadecene epoxides with fatty alcohols containing 16 to 18 carbon atoms are preferably used. If polyols are used instead of the fatty alcohols for the ring opening reaction, they are selected for example from the following substances: glycerol; alkylene glycols such as, for example, ethylene glycol, diethylene glycol, propylene glycol, butylene glycol, hexylene glycol and polyethylene glycols with an average molecular weight of 100 to 1,000 dalton; technical oligoglycerol mixtures with a degree of self-condensation of 1.5 to 10 such as, for example, technical diglycerol mixtures with a diglycerol content of 40 to 50% by weight; methylol compounds such as, in particular, trimethylol ethane, trimethylol propane, trimethylol butane, pentaerythritol and dipentaerythritol; lower alkyl glucosides, more particularly those containing 1 to 8 carbon atoms in the alkyl chain such as, for example, methyl and butyl glucoside; sugar alcohols containing 5 to 12 carbon atoms such as, for example, sorbitol or mannitol, sugars containing 5 to 12 carbon atoms such as, for example, glucose or sucrose; amino sugars such as, for example, glucamine.

Emulsifiers

Suitable emulsifiers (component b) are, for example, nonIonic surfactants from at least one of the following groups:

(b1) products of the addition of 2 to 30 mol ethylene oxide and/or 0 to 5 mol propylene oxide onto linear fatty alcohols containing 8 to 22 carbon atoms, onto fatty acids containing 12 to 22 carbon atoms, onto alkylphenols containing 8 to 15 carbon atoms in the alkyl group and onto alkylamines containing 8 to 22 carbon atoms in the alkyl group;

(b2) alkyl mono- and oligoglycosides containing 8 to 22 carbon atoms in the alkyl group and ethoxylated analogs thereof;

(b3) products of the additon of 15 to 60 mol ethylene oxide onto castor oil and/or hydrogenated castor oil;

(b4) products of the addition of 2 to 15 mol ethylene oxide onto castor oil and/or hydrogenated castor oil;

(b5) mono-, di- and trialkyl phosphates and mono-, di- and/or tri-PEG-alkyl phosphates and salts thereof;

(b6) wool wax alcohols;

(b7) polysiloxane/polyalkyl polyether copolymers and corresponding derivatives;

(b8) polyalkylene glycols and (b9) glycerol carbonate.

The addition products of ethylene oxide and/or propylene oxide onto fatty alcohols, fatty acids, alkylphenols or onto castor oil are known commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide onto glycerol are known as refatting agents for cosmetic preparations from DE 20 24 051 PS. $C_{8/18}$ alkyl mono- and oligoglycosides, their production and their use are known from the prior art. They are produced in particular by reacting glucose or oligosaccharides with primary $C_{8-18}$ alcohols. So far as the glycoside unit is concerned, both monoglycosides in which a cyclic sugar unit is attached to the fatty alcohol by a glycoside bond and oligomeric glycosides with a degree of oligomerization of preferably up to about 8 are suitable. The degree of oligomerization is a statistical mean value on which the homolog distribution typical of such technical products is based.

In addition, zwitterionic surfactants may be used as emulsifiers. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocoamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-coco-alkylaminopropionate, cocoacylaminoethyl aminopropionate and $C_{12/18}$ acyl sarcosine.

Finally, cationic surfactants are also suitable emulsifiers, those of the esterquat type, preferably methyl-quaternized difatty acid triethanolamine ester salts, being particularly preferred.

Polyol Esters

Polyol esters which—as co-emulsifiers—form component (c) may be selected from the following groups of compounds:

(c1) partial esters of glycerol and/or sorbitan with unsaturated, linear or saturated, branched fatty acids containing 12 to 22 carbon atoms and/or hydroxycarboxylic acids containing 3 to 18 carbon atoms and adducts thereof with 1 to 30 mol of ethylene oxide;

(c2) partial esters of polyglycerol (average degree of self-condensation 2 to 8), polyethylene glycol (molecular weight 400 to 5000), trimethylolpropane, pentaerythritol, sugar alcohols (for example sorbitol), alkyl glucosides (for example methyl glucoside, butyl glucoside, lauryl glucoside) and polyglucosides (for example cellulose) with saturated and/or unsaturated, linear or branched fatty acids containing 12 to 22 carbon atoms and/or hydroxycarboxylic acids containing 3 to 18 carbon atoms and adducts thereof with 1 to 30 mol ethylene oxide;

(c3) mixed esters of pentaerythritol, fatty acids, citric acid and fatty alcohol according to DE 11 65 574 PS and/or mixed esters of fatty acids containing 6 to 22 carbon atoms, methyl glucose and polyols, preferably glycerol or polyglycerol.

Typical examples of suitable partial glycerids are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30 and preferably 5 to 10 mol ethylene oxide with the partial glycerides mentioned are also suitable.

Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxy-stearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitah sesquimaleate, sorbitan dimaleate, sorbitan trimaleate and technical mixtures thereof. Addition products of 1 to 30 and preferably 5 to 10 mol ethylene oxide onto the sorbitan esters mentioned are also suitable.

Typical examples of suitable polyglycerol esters are Polyglyceryl-2 Dipolyhydroxystearate (Dehymuls® PGPH), Polyglycerin-3-Diisostearate (Lameform® TGI), Polyglyceryl-4 Isostearate (Isolan® GI 34), Polyglyceryl-3 Oleate, Diisostearoyl Polyglyceryl-3 Diisostearate (Isolan® PDI), Polyglyceryl-3 Methylglucose Distearate (Tego Care® 450), Polyglyceryl-3 Beeswax (Cera Bellina®), Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admule® WOL 1403), Polyglyceryl Dimerate Isostearate and mixtures thereof.

Examples of other suitable polyolesters are the mono-, di- and triesters of trimethylol propane or pentaerythritol with lauric acid, cocofatty acid, tallow fatty acid, palmitic acid, stearic acid, oleic acid, behenic acid and the like optionally reacted with 1 to 30 mol ethylene oxide.

Polyols

In a preferred embodiment of the invention, the concentrates may additionally contain polyols as an optional component (d) for reducing viscosity. Suitable polyols preferably contain 2 to 15 carbon atoms and at least two hydroxyl groups. The polyols may contain other functional groups, more especially amino groups, or may be modified with nitrogen. Typical examples are glycerol;

alkylene glycols such as, for example, ethylene glycol, diethylene glycol, propylene glycol, butylene glycol, hexylene glycol and polyethylene glycols with an average molecular weight of 100 to 1000 dalton;

technical oligoglycerol mixtures with a degree of self-condensation of 1.5 to 10 such as, for example, technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms, for example sorbitol or mannitol;

sugars containing 5 to 12 carbon atoms, for example glucose or sucrose;

amino sugars, for example glucamine;

dialcoholamines, such as diethanolamine or 2-aminopropane-1,3-diol.

The polyols are used in quantities of typically 0.1 to 15 and preferably 0.5 to 5% by weight. If larger quantities of polyol, preferably glycerol or ethylene glycol, are used, the concentrates are simultaneously stabilized against microbial infestation.

Production Process

In one preferred embodiment, which is also a subject of the invention, the pearlizing concentrates are produced by preparing a mixture of components (a), (b), (c) and optionally (d), heating it to a temperature 1 to 30° C. above the melting point of the mixture, mixing it with the necessary quantity of water having substantially the same temperature and then cooling the mixture to room temperature. In an alternative method of production, a concentrated aqueous (anionic) surfactant paste may be initially introduced, the pearlizing wax stirred in while heating and the mixture subsequently diluted with more water to the required concentration or the mixing step may be carded out in the presence of polymeric hydrophilic thickeners such as, for example, hydroxypropyl celluloses, xanthan gum or polymers of the Carbomer type.

Commercial Applications

The pearlizing concentrates according to the invention are suitable for opacifying surface-active preparations such as, for example, hair shampoos or manual dishwashing detergents. To produce opacified and pearlescent, liquid water-based preparations of water-soluble surfctants, the pearlizing concentrates are added to the clear water-based preparations in a quantity of 0.5 to 40 and preferably 1 to 20% by weight, normally at 0 to 40° C., and are distributed therein by stirring. Finally, the present invention also relates to the use of polyol esters as viscosity adjusters for the production of pearlizing concentrates with active substance contents of at elast 55% by weight.

Cosmetic and/or Pharmaceutical Preparations

The pearlizing concentrates according to the invention may be used for the production of cosmetic and/or pharmaceutical preparations, for example hair shampoos, hair lotions, foam baths, shower baths, creams, gels, lotions, alcoholic and aqueous/ alcoholic solutions, emulsions, wax/fat compounds, stick preparations, powders or ointments. These preparations may also contain mild surfactants, oil components, emulsifiers, superfatting agents, consistency factors, thickeners, polymers, silicone compounds, fats, waxes, stabilizers, biogenic agents, deodorizers, antiperspirants, anti-dandruff agents, film formers, swelling agents, UV protection factors, antioxidants, hydrotropes, preservatives, insect repellents, self-tanning agents, solubilizers, perfume oils, dyes and the like as further auxiliaries and additives.

Typical examples of suitable mild, i.e. particularly dermatologically compatible, surfactants are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, α-olefin sulfonates, ether carboxylic acids, alkyl oligoglucosides, fatty acid glucamides, alkylamidobetaines and/or protein fatty acid condensates, preferably based on wheat proteins.

Suitable oil components are, for example, Guerbet alcohols based on fatty alcohols containing 6 to 18 and preferably 8 to 10 carbon atoms, esters of linear $C_{6-22}$ fatty acids with linear $C_{6-22}$ fatty alcohols, esters of branched $C_{6-13}$ carboxylic acids with linear $C_{6-22}$ fatty alcohols such as, for example, myristyl myristate, myristyl palmitate, myristyl stearate, myristyl isostearate, myristyl oleate, myristyl behenate, myristyl enucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and enucyl erucate. Also suitable are esters of linear $C_{6-22}$ fatty acids with branched alcohols, more particularly 2-ethyl hexanol, esters of hydroxycarboxylic acids with linear or branched $C_{6-22}$ fatty alcohols, more especially Dioctyl Malate, esters of linear and/or branched fatty acids with polyhydric alcohols (for example propylene glycol, dimer diol or trimer triol) and/or Guerbet alcohols, triglycerides based on $C_{6-10}$ fatty acids, liquid mono-/di-/tri-glyceride mixtures based on $C_{6-18}$ fatty acids, esters of $C_{6-22}$ fatty alcohols and/or Guerbet alcohols with aromatic carboxylic acids, more particularly benzoic acid, esters of $C_{2-12}$ dicarboxylic acids with linear or branched alcohols containing 1 to 22 carbon atoms or polyols containing 2 to 10 carbon atoms and 2 to 6 hydroxyl groups, vegetable oils, branched primary alcohols, substituted cyclohexanes, linear and branched $C_{6-22}$ fatty alcohol carbonates, Guerbet carbonates, esters of benzoic acid with linear and/or branched $C_{6-22}$ alcohols (for example Finsolv® TN), linear or branched, symmetrical or nonsymmetrical dialkyl ethers containing 6 to 22 carbon atoms per alkyl group, ring opening products of epoxidized fatty acid esters with polyols, silicone oils and/or aliphatic or naphthenic hydrocarbons, for example squalane, squalene or dialkyl cyclohexanes.

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used.

Suitable thickeners are, for example, Aerosil types (hydrophilic silicas), polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates or alkyl oligoglucosides and electrolytes, such as sodium chloride and ammonium chloride.

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grünau), quaternized wheat polypeptides, polyethyleneimine, cationic silicone polymers such as, for example, amodimethicone, copolymers of adipic acid and dimethylamino-hydroxypropyl diethylenetriamine (Cartaretine®, Sandoz), copolymers of acrylic acid with dimethyl diallyl ammonium chloride (Merquat® 550, Chemviron), polyaminopolyamides as described, for example, in FR 2 252 840 A and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar®CBS, Jaguar®C-17, Jaguar®C-16 of Celanese, quaternized ammonium salt polymers such as, for example, Mirapol® A-15, Mirapol® AD-1, Mirapol® AZ-1 of Miranol.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

Suitable silicone compounds are, for example, dimethyl polysiloxanes methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates. A detailed overview of suitable volatile silicones can be found in Todd et al. in Cosm. Toil. 91, 27 (1976).

Typical examples of fats are glycerides while suitable waxes are inter alia natural waxes such as, for example, candelilla wax, carnauba wax, Japan wax, espartograss wax, cork wax, guamuma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes, microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes.

Metal salts of fatty acids such as, for example, magnesium, aluminium and/or zinc stearate or ricinoleate may be used as stabilizers.

In the context of the invention, biogenic agents are, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes.

Cosmetic deodorants counteract, mask or eliminate body odors. Body odors are formed through the action of skin bacteria on apocrine perspiration which results in the formation of unpleasant-smelling degradation products. Accordingly, deodorants contain active principles which act as germ inhibitors, enzyme inhibitors, odor absorbers or odor maskers.

Basically, suitable germ inhibitors are any substances which act against gram-positive bacteria such as, for example, 4-hydroxybenzoic acidand salts and esters thereof, N-(4-chlorophenyl)N'-(3,4-dichlorophenyl)-urea, 2,4,4'-trichloro-2'-hydroxydiphenylether (triclosan), 4-chloro-3,5-dimethylphenol, 2,2'-methylene-bis-(6-bromo-4-chlorophenol), 3methyl4-(1-methylethyl)-phenol, 2-benzyl4-chlorophenol, 3-(4-chloro -phenoxy)-propane-1, 2-diol, 3-iodo-2-propinyl butyl carbamate, chlorhexidine, 3,4,4'-trichlorocarbanilide (TTC), antibacterial perfumes, thymol, thyme oil, eugenol, nettle oil, menthol, mint oil, farnesol, phenoxyethanol, glycerol monolaurate (GML), diglycerol monocaprate (DMC), salicylic acid -N-alkylamides such as, for example, salicylic acid-n-octyl amide or salicylic acid-n-decyl amide.

Suitable enzyme inhibitors are, for example, esterase inhibitors. Esterase inhibitors are preferably trialkyl citrates, such as trimethyl citrate, tripropyl citrate, triisopropyl citrate, tributyl citrate and, in particular, triethyl citrate (Hydagen® CAT, Henkel KGaA, Düsseldorf, FRG). Esterase inhibitors inhibit enzyme activity and thus reduce odor formation. Other esterase inhibitors are sterol sulfates or phosphates such as, for example, lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof, for example citric acid, malic acid, tartaric acid or tartaric acid diethyl ester, and zinc glycinate.

Suitable odor absorbers are substances which are capable of absorbing and largely retaining the odor-forming compounds. They reduce the partial pressure of the individual components and thus also reduce the rate at which they spread. An important requirement in this regard is that perfumes must remain unimpaired. Odor absorbers are not active against bacteria. They contain, for example, a complex zinc salt of ricinoleic acid or special perfumes of largely neutral odor known to the expert as "fixateurs" such as, for example, extracts of labdanum or styrax or certain abietc acid derivatives as their principal component. Odor maskers are perfumes or perfume oils which, besides their odor-masking function, impart their particular perfume note to the deodorants. Suitable perfume oils are, for example, mixtures of natural and synthetic fragrances. Natural fragrances include the extracts of blossoms, stems and leaves, fruits, fruit peel, roots, woods, herbs and grasses, needles and branches, resins and balsams. Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, p-tert.butyl cyclohexylacetate, linalyl acetate, phenyl ethyl acetate, linalyl benzoate, benzyl formate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxy-citronellal, lilial and bourgeonal. Examples of suitable ketones are the ionones and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evemyl, iraldein gamma, phenylacetic acid, geranyl acetate, benzyl acetate, rose oxide, romillat, irotyl and floramat.

Antiperspirants reduce perspiration and thus counteract underarm wetness and body odor by influencing the activity of the eccrine sweat glands. Aqueous or water-free antiperspirant formulations typically contain the following ingredients:

(a) astringent active principles,
(b) oil components,
(c) nonionic emulsifiers,
(d) co-emulsifiers,
(e) consistency factors,
(f) auxiliaries in the form of, for example, thickeners or complexing agents and/or
(g) nonaqueous solvents such as, for example, ethanol, propylene glycol and/or glycerol.

Suitable astringent active principles of antiperspirants are, above all, salts of aluminium, zirconium or zinc. Suitable antihydrotic agents of this type are, for example, aluminium chloride, aluminium chlorohydrate, aluminium dichlorohydrate, aluminium sesquichlorohydrate and complex compounds thereof, for example with 1,2-propylene glycol, aluminium hydroxyallantoinate, aluminium chloride tartrate, aluminium zirconium trichlorohydrate, aluminium zirconium tetrachlorohydrate, aluminium zirconium pentachlorohydrate and complex compounds thereof, for example with amino acids, such as glycine. Oil-soluble and water-soluble auxiliaries typically encountered in antiperspirants may also be present in relatively small amounts. Oil-soluble auxiliaries such as these include, for example,

- inflammation-inhibiting, skin-protecting or pleasant-smelling essential oils,
- synthetic skin-protecting agents and/or
- oil-soluble perfume oils.

Typical water-soluble additives are, for example, preservatives, water-soluble perfumes, pH regulators, for example buffer mixtures, water-soluble thickeners, for example water-soluble natural or synthetic polymers such as, for example, xanthan gum, hydroxyethyl cellulose, polyvinyl pyrrolidone or high molecular weight polyethylene oxides.

Suitable antidandruff agents are climbazol, octopirox and zinc pyrithione.

Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

Suitable swelling agents for aqueous phases are montmorillonites, clay minerals, Pemulen and alkyl-modified Carbopol types (Goodrich). Other suitable polymers and swelling agents can be found in R. Lochhead's review in Cosm. Toil. 108, 95 (1993).

Examples of UV protection factors include organic substances (light filters) which are liquid or crystalline at room temperature and which are capable of absorbing ultraviolet radiation and of releasing the energy absorbed in the form of longer-wave radiation, for example heat. UV-B filters can be oil-soluble or water-soluble. The following are examples of oil-soluble substances:

3-benzylidene camphor or 3-benzylidene norcamphor and derivatives thereof, for example 3-(4-methylbenzylidene)-camphor, as described in EP 0693471 B1;
4-aminobenzoic acid derivatives, preferably 4-(dimethylamino)-benzoic acid-2-ethylhexyl ester, 4-(dimethylamino)-benzoic acid-2-octyl ester and 4-(dimethylamino)-benzoic acid amyl ester;
esters of cinnamic acid, preferably 4-methoxycinnamic acid-2-ethylhexyl ester, 4-methoxycinnamic acid propyl ester, 4-methoxycinnamic acid isoamyl ester, 2-cyano-3,3-phenylcinnamic acid-2-ethylhexyl ester (Octocrylene);
esters of salicylic acid, preferably salicylic acid-2-ethylhexyl ester, salicylic acid-4-isopropylbenzyl ester, salicylic acid homomenthyl ester;
derivatives of benzophenone, preferably 2-hydroxy-4-methoxybenzo-phenone, 2-hydroxy-4-methoxy-4'-methylbenzophenone, 2,2'-dihydroxy-4-methoxybenzophenone;
esters of benzalmalonic acid, preferably 4-methoxybenzalmalonic acid di-2-ethylhexyl ester;
triazine derivatives such as, for example, 2,4,6-trianilino-(p-carbo-2'-ethyl-1'-hexyloxy)-1,3,5-triazine and Octyl Triazone, as described in EP 0 818 450 A1, or Dioctyl Butamido Triazine (Uvasorb® HEB);
propane-1,3-diones such as, for example, 1-(4-tert.butylphenyl)-3-(4'-methoxyphenyl)-propane-1,3-dione;
ketotricyclo(5.2.1)decane derivatives, as described in EP 0 694 521 B1.

Suitable water-soluble substances are 2-phenylbenzimidazole-5-sulfonic acid and alkali metal, alkaline earth metal, ammonium, alkylammonium, alkanolammonium and glucammonium salts thereof;
sulfonic acid derivatives of benzophenones, preferably 2-hydroxy-4-methoxybenzophenone-5-sulfonic acid and salts thereof;
sulfonic acid derivatives of 3-benzylidene camphor such as, for example, 4-(2-oxo-3-bornylidenemethyl)-benzene sulfonic acid and 2-methyl-5-(2-oxo-3-bornylidene)-sulfonic acid and salts thereof.

Typical UV-A filters are, in particular, derivatives of benzoyl methane such as, for example 1-(4'-tert.butylphenyl)-3-(4'-methoxyphenyl)-propane-1,3-dione, 4-tert-butyl-4'-methoxydibenzoylmethane (Parsol 1789), 1-phenyl-3-(4'-isopropylphenyl)-propane-1,3-dione and the eneamine compounds described in DE 19712033 A1 (BASF). The UV-A and UV-B filters may of course also be used in the form of mixtures. Besides the soluble substances mentioned, insoluble pigments, i.e. finely dispersed metal oxides or salts, may also be used for this purpose. Examples of suitable metal oxides are, in particular, zinc oxide and titanium dioxide and also oxides of iron, zirconium, silicon, manganese, aluminium and cerium and mixtures thereof. Silicates (talcum), barium sulfate and zinc stearate may be used as salts. The oxides and salts are used in the form of the pigments for skin-care and skin-protecting emulsions. The particles should have an average diameter of less than 100 nm, preferably from 5 to 50 nm and more preferably from 15 to 30 nm. They may be spherical in shape although ellipsoidal particles or other non-spherical particles may also be used. The pigments may also be surface-treated, i.e. hydrophilicized or hydrophobicized. Typical examples are coated titanium dioxides such as, for example, Titandioxid T 805 (Degussa) or Eusolex® T2000 (Merck). Suitable hydrophobic coating materials are, above all, silicones and particularly trialkoxyoctyl silanes or simethicones. So-called micro- or nanopigments are preferably used in sun protection products. Micronized zinc oxide is preferably used. Other suitable UV filters can be found in P. Finkel's review in SÖFW-Journal 122, 543 (1996).

Besides the two above-mentioned groups of primary protection factors, secondary protection factors of the antioxidant type may also be used. Secondary sun protection factors of the antioxidant type interrupt the photochemical reaction chain which is initiated when UV rays penetrate into the skin. Typical examples of suitable antioxidants are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotenoids, carotenes (for example α-carotene, β-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages (for example pmol to μmol/kg), also (metal) chelators (for example α-hydroxyfatty acids, palmitic acid, phytic acid, lactoferrine), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, α-glycosyl rutin, ferulic acid, furfurylidene glucitol, carnosine, butyl hydroxytoluene, butyl hydroxyanisole, nordihydroguaiac resin acid, nordihydroguaiaretic acid, trihydroxy-butyrophenone, uric acid and derivatives thereof, mannose and derivatives thereof, Superoxid-Dismutase, zinc and derivatives thereof (for example ZnO, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

In addition, hydrotropes, for example ethanol, isopropyl alcohol or polyols, may be used to improve flow behavior.

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive"). Suitable insect repellents are N,N-diethyl-m-toluamide, pentane-1,2-diol or Ethyl Butylacetyl-aminopropionate. A suitable self tanning agent is dihydroxy-acetone.

Suitable perfume oils are mixtures of natural and synthetic fragrances. Natural fragrances include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamon, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, α-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or In the form of mixtures: bergamot oil, dihydromyrcenol, lilial, lyral, citronellol, phenylethyl alcohol, α-hexylcinnamaldehyde, geraniol, benzyl acetone, 2 cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Suitable dyes are any of the substances suitable and approved for cosmetic purposes as listed, for example, in the publication "Kosmetische Färbemittel" of the Farbstoffkommission der Deutschen Forschungs-gemeinschaft, Verlag Chemie, Weinheim, 1984, pages 81 to 106. These dyes are normally used in concentrations of 0.001 to 0.1% by weight, based on the mixture as a whole.

The total percentage content of auxiliaries and additives may be from 1 to 50% by weight and is preferably from 5 to 40% by weight, based on the particular preparation. The prepartions may be produced by standard hot or cold processes and are preferably produced by the phase inversion temperature method.

EXAMPLES

Pearlizing concentrates 1 to 8 according to the invention and comparison mixture C1 were stored for 14 days at 40° C. after which their viscosities were determined by the Brookfield method in an RVT viscosimeter (23° C., 10 r.p.m., spindle 5). Water-based hair shampoo formulations containing 2 g of pearlizing concentrates 1 to 8 and C1, 15 g of cocofatty alcohol+2EO sulfate sodium salt, 3 g of dimethyl polysiloxane, 5 g of cocoalkyl glucoside and 1.5 g of an esterquat (water to 100% by weight) were then prepared by mixing the ingredients. The particle fineness of the pearlescent crystals in the hair shampoos was visually evaluated under a microscope on a scale of 1=very fine crystals to 5=coarse crystals. Pearlescence was also evaluated on a scale of 1=sparkling to 5=dull. Opacity was visually determined and evaluated as (+)=opaque or (−)=nonopaque. The compositions and results are set out in Table 1 where all quantities are in % by weight.

TABLE 1

Composition and performance of pearlizing concentrates

| Composition | 1 | 2 | 3 | 4 | 5 | 6 | 7 | 8 | C1 |
|---|---|---|---|---|---|---|---|---|---|
| Ethyleneglycol Distearate | 30.0 | — | — | 30.0 | 30.0 | 32.0 | 35.0 | 35.0 | 30.0 |
| Glyceryl Stearate | — | 30.0 | — | — | — | — | — | — | — |
| Distearyl Ether | — | — | 30.0 | — | — | — | — | — | — |
| Coco Glucosides | 15.0 | 15.0 | 17.0 | 15.0 | 15.0 | 15.0 | 15.0 | 15.0 | 32.0 |
| Laureth-4 | 12.0 | — | — | 12.0 | — | 12.0 | — | 12.0 | — |
| Cocamidopropyl Betaine | — | 12.0 | 11.0 | — | 10.0 | — | 10.0 | — | — |
| Sorbitan Oleate | 4.0 | — | — | — | 4.0 | — | — | — | — |
| PEG-3 Trimethylolpropane Distearate | — | 4.0 | — | — | — | 4.0 | — | — | — |
| Polyglyceryl-2 Dipolyhydroxystearate | — | — | 4.0 | — | — | — | 4.0 | — | — |
| Polyglycerin-3-Diisostearate | — | — | — | 4.0 | — | — | — | 4.0 | — |
| Glycerol | — | — | — | — | — | 2.0 | 2.0 | 2.0 | 6.0 |
| Water | | | | | to 100 | | | | |
| Viscosity of the concentrates [Pas] | | | | | | | | | |
| after 1 d, 40° C. | 11 | 14 | 13 | 12 | 13 | 12 | 14 | 14 | 42 |
| after 14 d, 40° C. | 11 | 14 | 13 | 12 | 13 | 12 | 14 | 14 | 40 |
| Pearlescence in the formulation | | | | | | | | | |
| Sparkle | 1.5 | 1.5 | 1.0 | 1.0 | 1.5 | 1.5 | 1.0 | 1.0 | 2.0 |
| Particle fineness | 1.5 | 1.5 | 1.5 | 2.0 | 1.5 | 1.0 | 1.0 | 1.5 | 3.0 |
| Opacity | — | — | — | — | — | — | — | — | + |

What is claimed is:

1. A highly concentrated flowable pearlizing concentrate comprising: (a) from about 25 to about 45% by weight of a pearlizing wax selected from the group consisting of an alkylene glycol ester, a fatty acid alkanolamide, a partial glyceride ester of a polybasic carboxylic acid, a partial glyceride ester of a polybasic hydroxysubstituted carboxylic acid, a fatty alcohol, a fatty acid, a fatty ketone, a fatty aldehyde, a fatty ether, a fatty carbonate, ring opening products of olefin epoxides and mixtures thereof; (b) from about 25 to about 40% by weight of nonionic, amphoteric, zwitterionic and/or cationic emulsifier and; (c) from about 0.5 to about 15% by weight of a polyol ester and the remainder water wherein the sum of components (a), (b) and (c) is at least 55% by weight.

2. The concentrate of claim 1 wherein the nonionic surfactant is selected from the group consisting of adducts of from about 2 to about 30 moles of ethylene glycol, from 0 to about 5 moles of propylene glycol or a combination thereof with linear fatty alcohols having from about 8 to about 22 carbon atoms or fatty acids having from about 12 to about 22 carbon atoms or alkyl phenols having from about 8 to about 15 carbon atoms in the alkyl group or alkyl amines having from about 8 to about 22 carbon atoms in the alkyl group; alkyl mono- and olioglycosides having from about 8 to about 22 carbon atoms in the alkyl group; addition products of castor oil or hydrogenated castor oil and from about 1 to about 1.5 moles of ethylene oxide or from about 15 to about 60 moles ethylene oxide; a di- or tri- PEG alkyl phosphate and salts thereof; a wool wax alcohol; a copolymr of polysiloxane and a polyalkyl ther; a polyalkylene glycol; a glycerol carbonate.

3. The concentrate of claim 1 wherein component (c) is cocamidopropyl Betaine and/or an esterquat.

4. The concentrate of claim 1 wherein component (c) is selected from the group consisting of a partial ester of glycerol or sorbitan wherein the acid portion of the ester is a saturated or unsaturated, linear or branched fatty acid having from about 12 to about 22 carbon atoms or a hydroxy-substituted carboxylic acid having from about 3 to about 18 carbon atoms and adducts thereof having 1 to about 30 moles of ethylene oxide; a partial ester of polyglycerol, polyethylene glycol, trimethylol propane, pentaerythritol, an alkyl polylglucoside wherein the acid portion of the ester is a saturated or unsaturated, linear or branched fatty acid having from about 12 to about 22 carbon atoms or a hydroxy-substituted carboxylic acid having from about 3 to about 18 carbon atoms and adducts thereof having 1 to about 30 moles of ethylene oxide; mixed eaters of pentaerythritol, fatty alcohols and fatty acids and citric acid; mixed esters of fatty acids having from about 6 to about 22 carbon atoms; a mixture of methyl glucose and a polyol.

5. The concentrate of claim 1 further comprising a polyol.

6. The concentrate of claim 5 wherein the polyol is glycerol and/or ethylene glycol.

7. The concentrate of claim 6 wherein the amount of the polyol in the concentrate is from about 0.1 to about 15% by weight of the concentrate.

8. A process for the production of the pearlizing conc ntrate of claim 1 comprising heating a mixture of components (a), (b), (c) and optionally (d) to a temperature of from about 1 to about 30° C. above the melting point of the mixture; (2) adding a quantity of water to the mixture sufficient to result in a concentrate of a predetermined water content; (3) cooling the composition of step (2) to room temperature.

9. A process for increasing the viscosity of a pearlesecent concentrate having an active substance content of at least 55% by weight comprising adding a viscosity increasing effective amount of a polyol ester to the pearlescent concentrate.

* * * * *